US012808863B2

(12) United States Patent
Guerrero Navarro

(10) Patent No.: US 12,808,863 B2
(45) **Date of Patent: *Nov. 24, 2026**

(54) METHODS TO IMPROVE DETECTION OF GLYCOSYLAMINES

(71) Applicant: Agilent Technologies, Inc., Santa Clara, CA (US)

(72) Inventor: Andres Guerrero Navarro, Pamplona (ES)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 1102 days.

This patent is subject to a terminal disclaimer.

(21) Appl. No.: 17/606,915

(22) PCT Filed: Apr. 30, 2020

(86) PCT No.: PCT/US2020/030826
§ 371 (c)(1),
(2) Date: Oct. 27, 2021

(87) PCT Pub. No.: WO2020/227027
PCT Pub. Date: Nov. 12, 2020

(65) Prior Publication Data

US 2022/0214334 A1 Jul. 7, 2022

Related U.S. Application Data

(60) Provisional application No. 62/842,809, filed on May 3, 2019.

(51) Int. Cl.
*C07H 5/06* (2006.01)
*G01N 30/06* (2006.01)
(Continued)

(52) U.S. Cl.
CPC ........... *G01N 33/533* (2013.01); *G01N 30/06* (2013.01); *G01N 2030/027* (2013.01); *G01N 2333/98* (2013.01); *G01N 2440/38* (2013.01)

(58) Field of Classification Search
CPC ................ G01N 33/533; G01N 30/06; G01N 2030/027; G01N 2333/98; G01N 2440/38
See application file for complete search history.

(56) References Cited

U.S. PATENT DOCUMENTS 8,828,732 B2 9/2014 Abe et al.
10,151,759 B2 12/2018 Wuhrer et al.
(Continued)

FOREIGN PATENT DOCUMENTS

CN 101120254 A 2/2008
CN 102144164 A 8/2011
(Continued)

OTHER PUBLICATIONS

Cook, K. Steven, Kevin Bullock, and Timothy Sullivan. "Development and qualification of an antibody rapid deglycosylation method. " Biologicals 40.2 (2012): 109-117. (Year: 2012).*
(Continued)

*Primary Examiner* — Bao-Thuy L Nguyen
(74) *Attorney, Agent, or Firm* — Lando & Anastasi, LLP

(57) ABSTRACT

The present invention provides methods to improve the sensitivity of detecting glycosylamines released from glycoconjugates, such as glycoproteins or glycopeptides, by enzymatic digestion when labeling them with amine-reactive dyes.

20 Claims, 2 Drawing Sheets

(51) Int. Cl.
*G01N 33/533* (2006.01)
*G01N 30/02* (2006.01)

(56) References Cited

U.S. PATENT DOCUMENTS

| | | | |
|---|---|---|---|
| 11,543,414 B2 * | 1/2023 | Guerrero Navarro ........................ G01N 1/4077 | |
| 2002/0051971 A1 | 5/2002 | Stuelpnagel et al. | |
| 2008/0227092 A1 | 9/2008 | Lohse et al. | |
| 2010/0047828 A1 | 2/2010 | Sorensen et al. | |
| 2010/0233034 A1 | 9/2010 | Olivier et al. | |
| 2012/0244625 A1 | 9/2012 | Ruhaak et al. | |
| 2013/0171658 A1 | 7/2013 | Fulton | |
| 2014/0038215 A1 | 2/2014 | Smart et al. | |
| 2016/0025606 A1 | 1/2016 | Oroskar et al. | |
| 2018/0156809 A1 | 6/2018 | Kimzey et al. | |
| 2019/0041384 A1 | 2/2019 | Haxo et al. | |

FOREIGN PATENT DOCUMENTS

| | | | | |
|---|---|---|---|---|
| CN | 102770765 | A | 11/2012 | |
| CN | 103458983 | A | 12/2013 | |
| EP | 2282209 | A1 | 2/2011 | |
| WO | 2011009893 | A1 | 1/2011 | |
| WO | 2011038873 | A1 | 4/2011 | |
| WO | 2012037407 | A1 | 3/2012 | |
| WO | WO 2012107572 | A1 | 8/2012 | |
| WO | 2016003795 | A1 | 1/2016 | |
| WO | 2016100447 | A1 | 6/2016 | |
| WO | WO-2018035271 | A1 * | 2/2018 | ............. C09B 19/00 |
| WO | WO 2018175800 | A1 | 9/2018 | |

OTHER PUBLICATIONS

Ruhaak, L. Renee, et al. "Hydrophilic interaction chromatography-based high-throughput sample preparation method for N-glycan analysis from total human plasma glycoproteins." Analytical chemistry 80.15 (2008): 6119-6126. (Year: 2008).*

Ruhaak, L. Radius, et al. "Glycan labeling strategies and their use in identification and quantification." Analytical and bioanalytical chemistry 397.8 (2010): 3457-3481. (Year: 2010).*

Vainauskas, Saulius, et al. "A novel broad specificity fucosidase capable of core Î±1-6 fucose release from N-glycans labeled with urea-linked fluorescent dyes." Scientific reports 8.1 (2018): 9504. (Year: 2018).*

Vreeker, Gerda CM, and Manfred Wuhrer. "Reversed-phase separation methods for glycan analysis." Analytical and bioanalytical chemistry 409.2 (2017): 359-378. (Year: 2017).*

Zaikina, I., International Search Report, PCT/US2020/030826, Jul. 30, 2020, ISA/RU, Moscow, Russia.

Zaikina, I., Written Opinion, PCT/US2020/030826, Jul. 20, 2020, ISA/RU, Moscow, Russia.

Extended European Search Report from corresponding European Application No. 18771481.1 dated Dec. 15, 2020.

Kuan Jiang et al: "Solid-phase reductive amination for glycomic analysis", Analytica Chimica ACTA, vol. 962, Jan. 31, 2017 (Jan. 31, 2017), pp. 32-40, XP55752873, Amsterdam, NL, ISSN: 0003-2670, DOI: 10.1016/j.aca.2017.01.049.

Anonymous: "Solid Phase Extraction Products Improve Sensitivity and Increase Throughput," Jan. 1, 2015 (Jan. 1, 2015), XP055754609, Retrieved from the Internet: URL:https://www.sigmaaldrich.com/content/d am/sigma-aldrich/docs/Supelco/General_Info rmation/t402150.pdf [retrieved on Nov. 27, 2020].

Jana Svacinova et al: "A new approach for cytokinin isolation from Arabidopsis tissues using miniaturized purification: pipette tip solid-phase extraction," Plant Methods, vol. 8, No. 1, Jan. 1, 2012 (Jan. 1, 2012), p. 17, XP055543147, GB, ISSN: 1746-4811, DOI: 10.1186/1746-4811-8-17.

Anonymous: "AdvanceBio N-Glycan Sample Preparation Kit User Guide (96 samples) p/n 5190-8005," Feb. 24, 2015 (Feb. 24, 2015), XP055756514, Retrieved from the Internet: URL:https://www.agilent.com/cs/library/use rmanuals/public/AdvanceBio%20N-Glycan-96-5 991-9561.pdf [retrieved on Dec. 4, 2020].

Ikegami et al.: "Highly efficient analysis of underivatized carbohydrates using monolithic-silica-based capillary hydrophilic interaction (HILIC) HPLC", Anal Bioanal Chem., vol. 391, No. 7, 2008, pp. 2533-2542, XP019621437.

Notification of Transmittal of the International Search Report and the Written Opinion of the International Searching Authority from corresponding PCT/US2018/023875 dated Aug. 1, 2018.

* cited by examiner

METHODS TO IMPROVE DETECTION OF GLYCOSYLAMINES

CROSS-REFERENCE TO RELATED APPLICATIONS

This is a national stage application under 35 U.S.C. § 371 of International Application No. PCT/US2020/030826, filed Apr. 30, 2020, which is hereby incorporated by reference for all purposes. This application further claims priority to, and the benefit of, U.S. Provisional Patent Application No. 62/842,809, filed May 3, 2019, the contents of which are incorporated herein by reference for all purposes.

STATEMENT OF FEDERAL FUNDING

Not applicable.

BACKGROUND OF THE INVENTION

This invention relates to the field of improving the ability to detect glycosylamines labeled by amine-reactive dyes, particularly when the glycosylamines are in a solution containing other amines competing for labeling by the amine-reactive dye.

A number of commercial and regulatory requirements make it necessary to determine the nature and amount of glycans present on a glycoprotein or glycopeptide, and particularly for glycoproteins used as therapeutic agents. Since the glycans attached to the glycoprotein can affect characteristics critical to the glycoprotein's function, including its pharmacokinetics, stability, bioactivity, and immunogenicity, it is important to determine which ones are present. Characterization of glycans attached to biologics (such as therapeutic glycoproteins and vaccines) is required by the Food and Drug Administration to show composition of matter and consistency of manufacture, resulting in a need for extensive characterization of the product. Analysis of the profile of the carbohydrates is also important for quality control in the production of both therapeutic and non-therapeutic recombinant proteins, in which a change in carbohydrate profile may indicate stress in the system, signaling conditions that may require the contents of a commercial-scale fermenter to be discarded. There is therefore considerable interest by biochemists, clinical chemists, pharmaceutical manufacturers, and protein producers in determining the distribution profiles of glycans in biological samples, such as therapeutic glycoproteins.

Traditionally, carbohydrates have been labeled by reductive amination, using dyes suitable for labeling by that reaction. For example, reductive amination of N-glycans released from a glycoprotein by the deglycosylation enzyme PNGase F is typically accomplished by conjugating the free-reducing ends of the glycans to the free amino groups of a label, such as a fluorescent dye or a moiety with an electrical charge, such as 2-aminobenzamide, or "2-AB," as taught in U.S. Pat. No. 5,747,347. Depending on the label used, the labeled glycans can then be analyzed by any of a variety of analytical methods, such as high performance liquid chromatography ("HPLC"), capillary electrophoresis ("CE," including capillary zone electrophoresis, capillary gel electrophoresis, capillary isoelectric focusing, capillary isotachophoresis, and micellar electrokinetic chromatography), or microfluidic separation.

In recent years, several dyes, or labels (the terms are generally used interchangeably herein), have been developed that label carbohydrates, such as the N-glycans released from a glycoprotein by PNGase F, more quickly than traditional procedures. The action of PNGase F releases N-glycans in the form of glycosylamines. Dyes such as INSTANTPC® (ProZyme, Inc.) and RAPIFLUOR-MS® (Waters Corp.), are capable of reacting quickly with the glycosylamines released from glycoproteins. Unfortunately, the dyes also react with any other free amines (amines available to compete with the glycosylamines of interest for labeling by the amine-reactive dye) in the reaction solution, and many buffer solutions, such as Tris buffer contain free amines. This is a concern for the analysis of the glycans present on some glycoproteins, as considerations such as stability, pH, solubility, and cost may dictate the use of Tris buffers or other sources of free amines to ship or store the glycoproteins.

Therapeutic glycoproteins are expensive and some are available only in small quantities. The amount of glycans available for analysis is therefore often quite small, and may be on the order of picograms, while the amount of free amine in the solution may be orders of magnitude higher. The excess of amines from the buffer or other source compared to the glycans of interest can therefore sharply reduce the sensitivity of the assay. This is currently incompletely addressed by trying to avoid the use of buffers, such as Tris-containing buffers, that contain free amines, or by buffer exchange, which is tedious, not amenable to automation, and not always successful.

There remains a need in the art for methods that improve the sensitivity of labeling of glycosylamines by amine reactive dyes when they are provided in solutions that have free amines Surprisingly, the present invention meets these and other needs.

BRIEF SUMMARY OF THE INVENTION

The invention provides compositions, methods, systems, and kits, for improving the separation of labeled analytes by electrophoresis. In a first group of embodiments, the invention provides in vitro methods for labeling glycosylamines, and, optionally, for analyzing said labeled glycosylamines. The methods comprise the following steps in the following order: (a) obtaining glycosylamines in an aqueous solution, (b) mixing the aqueous solution in which glycosylamines are present with a quantity of organic solvent, thereby creating an organic solvent mixture composed of about 80% or more organic solvent, (c) passing the organic solvent mixture containing the glycosylamines through a porous solid support, thereby immobilizing the glycosylamines on the porous solid support, and, (d) labeling the glycosylamines with an amine-reactive dye, either (1) while the glycosylamines are immobilized on the porous solid support, and then eluting the labeled glycosylamines from the porous solid support with an aqueous solution into a container, or, (2) eluting the immobilized glycosylamines from the porous solid support with an aqueous solution into a container and then labeling the eluted glycosylamines with the amine-reactive dye, thereby labeling the glycosylamines. In some embodiments, the porous solid support is made of a hydrophilic material and the organic solvent mixture is about 80% to 95% organic solvent to about 20% to 5% aqueous solution. In some embodiments, the hydrophilic material is (a) cellulose, (b) glass fiber, (c) alumina, (d) silica, (e) a functionalized surface containing diol, aminopropyl, carbamoyl, cyanopropyl, ethylenediamine-N-propyl, (f) silica derivatized with diol, aminopropyl, or carbamoyl, (g) cellulose, (h) cyclodextrin, (i) aspartmamide, (j) triazole, (k) diethylaminoelthyl, (l) a resin used in solid phase extraction of carbohydrates, or, (m) a combination of two or more of these. In some embodiments, the solid support is made of silica and said silica is covalently bonded to one or more carbamoyl groups. In some embodiments, the silica is in the form of beads or particles. In some embodiments, the beads or particles are from 3-60 microns in size. In some embodiments, the beads or particles are about 30 microns in size. In some embodiments, the beads or particles covalently bonded to carbamoyl groups are Amide-80. In some embodiments, the porous solid support is in the form of a membrane. In some embodiments, the porous solid support is in the form of a monolith. In some embodiments, the porous solid support is in the form of beads. In some embodiments, the porous solid support is in the form of fibers. In some embodiments, the porous solid support is a resin. In some embodiments, the method further comprises step (c'), washing said porous solid support with a solution that is 80 to 90% organic solvent and 20 to 10% aqueous solution, between steps (c) and (d). In some embodiments, the method further comprises step (e), separating the labeled glycosylamines by subjecting them to a separation method. In some embodiments, the separation method subjects the labeled glycosylamines to high-performance liquid chromatography, ultra high-performance liquid chromatography, hydrophilic interaction liquid chromatography, capillary electrophoresis, microfluidic separation, or a combination of two or more of these, thereby separating the labeled glycosylamines. In some embodiments, the separated, labeled glycosylamines are analyzed by detecting fluorescence of the labels. In some embodiments, the separated, labeled glycosylamines are analyzed by mass spectrometry. In some embodiments, the organic solvent is acetonitrile, absolute ethanol, absolute methanol, isopropanol, butanol, toluene, ethyl acetate, acetone, tetrahydrofuran, diethyl ether, dichloromethane, chloroform, tert-buthyl-methyl ether, benzene, carbon tetrachloride, isooctane, hexane, or a combination of any two or more of these. In some embodiments, the organic solvent is acetonitrile. In some embodiments, the porous solid support is disposed in a well of a multi-well plate or microwell plate. In some embodiments, the solid support is disposed in a lumen of a microfluidic device. In some embodiments, the porous solid support is disposed in a centrifuge column or solid phase extraction cartridge. In some embodiments, the porous solid support is disposed in a centrifuge column. In some embodiments, the porous solid support has a surface of a non-hydrophilic material and the organic solvent mixture has 95% or more organic solvent. In some embodiments, the non-hydrophilic material is polyethylene, nylon, polyvinylidene fluoride, or polypropylene. In some embodiments, the porous solid support has pores or openings of 10 microns or smaller.

In a second group of embodiments, the invention provides kits for labeling with an amine-reactive dye glycosylamines released from a glycoprotein or glycopeptide with an enzyme. The kits comprise a deglycosylation enzyme, an aqueous solution suitable for incubating the deglycosylation enzyme with the glycoprotein or glycopeptide, an amine-reactive dye, an organic solvent, and a container having disposed within it a porous solid support. In some embodiments, the aqueous solution and the organic solvent are provided in the kit in pre-measured form such that, when combined, they form a mixture of organic solvent and aqueous solution that is 80-95% organic solvent to 20-5% aqueous solution. In some embodiments, the aqueous solution and the organic solvent are provided in the kit in pre-measured form such that, when combined, they form a mixture of organic solvent and aqueous solution that is 80-90% organic solvent to 20-10% aqueous solution. In some embodiments, the aqueous solution and the organic solvent are provided in pre-measured form such that, when combined, they form a mixture of organic solvent and aqueous solution that is 85%±2% organic solvent to 15%±2% aqueous solution. In some embodiments, the organic solvent is acetonitrile, absolute ethanol, absolute methanol, isopropanol, butanol, toluene, ethyl acetate, acetone, tetrahydrofuran, diethyl ether, dichloromethane, chloroform, tert-buthyl-methyl ether, benzene, carbon tetrachloride, isooctane, hexane, or a combination of any two or more of these. In some embodiments, the organic solvent is acetonitrile. In some embodiments, the deglycosylation enzyme is PNGase F. In some embodiments, the kit further comprises a denaturant. In some embodiments, the porous solid support is a hydrophilic material. In some embodiments, the porous solid support is in the form of a membrane. In some embodiments, the hydrophilic material is (a) cellulose, (b) glass fiber, (c) alumina, (d) silica, (e) a functionalized surface containing diol, aminopropyl, carbamoyl, cyanopropyl, ethylenediamine-N-propyl, (f) silica derivatized with diol, aminopropyl, or carbamoyl, (g) cellulose, (h) cyclodextrin, (i) aspartmamide, (j) triazole, (k) diethylaminoelthyl, (l) a resin used in solid phase extraction of carbohydrates, or, (m) a combination of two or more of these. In some embodiments, the solid support is made of silica and said silica is covalently bonded to one or more carbamoyl groups. In some embodiments, the solid support is made of silica and the silica is in the form of beads or particles. In some embodiments, the beads or particles are from 3-60 microns in size. In some embodiments, the beads or particles are about 30 microns in size. In some embodiments, the beads or particles covalently bonded to carbamoyl groups are Amide-80.

DETAILED DESCRIPTION

Introduction

Figure 1:
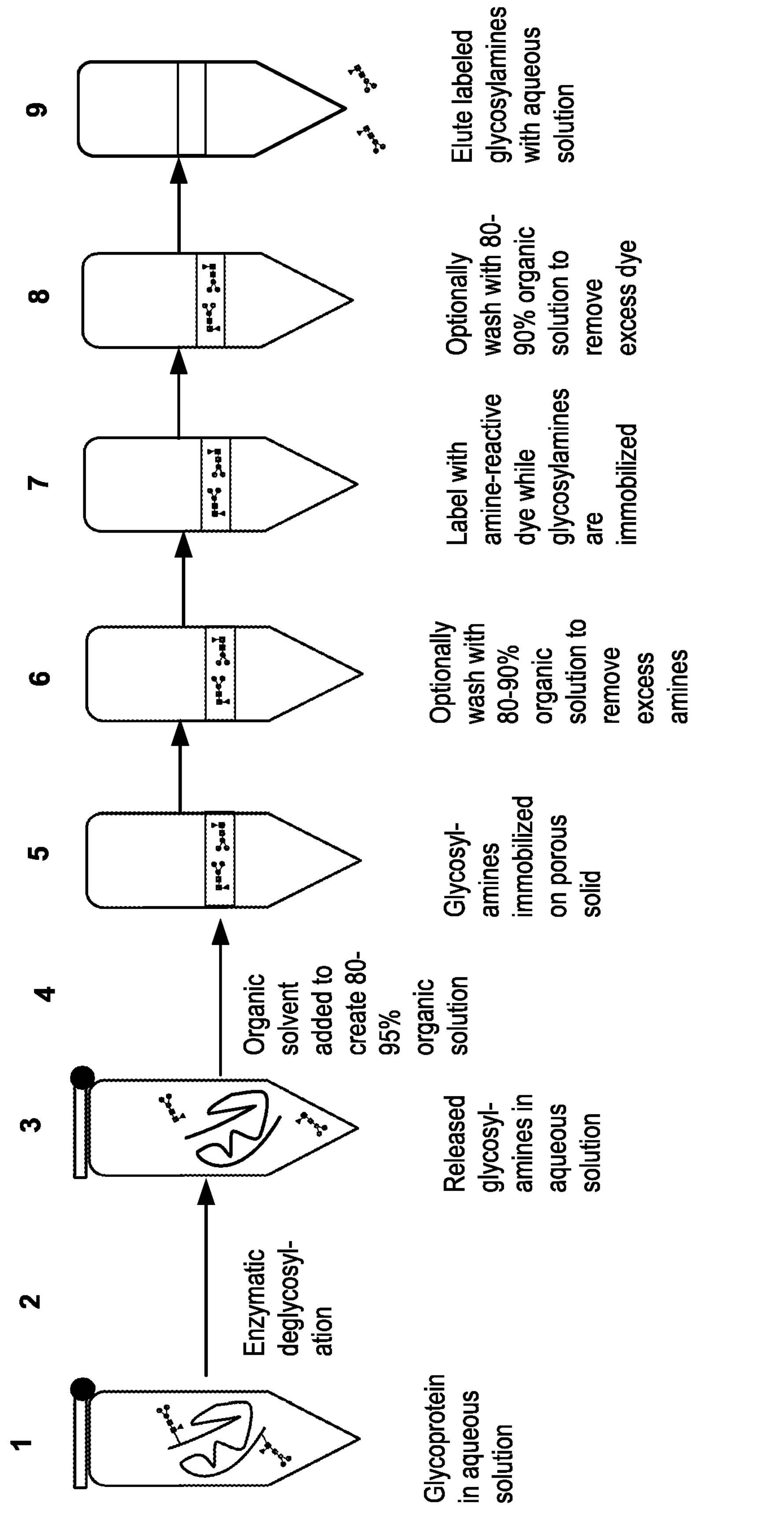
FIG. 1 is a diagram showing exemplar embodiments of some of the inventive methods. Number 1 shows a vial holding a glycoprotein in an aqueous solution. The protein moiety is shown as a solid line, while the glycans are shown as standard geometric figures representing different sugar moieties. The attachment of each glycan to the protein moiety is represented by a line thinner than the one representing the protein moiety. Following enzymatic digestion by PNGase F, designated by the number 2 on the Figure, number 3 shows the vial now holding the aglycosylated protein, represented by the same solid line as before, and glycosylamines released from the protein by the enzyme, represented by geometric shapes. Number 4 designates the addition of organic solvent to the starting aqueous solution in a quantity sufficient to create an organic solvent/aqueous solution mixture that is 80% to 95% organic solvent and 20% to 5% aqueous solution (note: although the caption states the organic solvent is added to form an 80% to 95% solution, the mixture of organic solvent to aqueous solution containing the glycosylamines is referred to in the specification as the "organic solvent mixture"). In the exemplar embodiment shown, the organic solvent mixture is then passed through a porous solid support made of a hydrophilic material and disposed in a second container. As shown in number 5, the glycosylamines have been retained and immobilized on the porous solid support in the second container, while the organic solvent mixture has flowed through and, having exited the container, is no longer in contact with the immobilized glycosylamines Number 6 shows an optional wash step in which the immobilized glycosylamines are washed with a solution that is 80 to 95% organic solvent/20 to 5% aqueous solution, to reduce the number of amines present that are not on the immobilized glycosylamines or otherwise retained on the solid support. Number 7 shows an embodiment in which the immobilized glycosylamines are labeled with an amine-reactive dye while immobilized on the porous solid support. Number 8 shows an optional wash step in which the labeled, immobilized glycosylamines are washed with a solution that is 80 to 95% organic solvent/20 to 5% aqueous solution to remove any excess dye. Number 9 shows the labeled, immobilized glycosylamines being eluted from the porous solid support by an aqueous solution.

As set forth in the Background, analysis of the kind and quantity of glycans attached to glycoproteins has become important for various regulatory and quality control purposes. In particular, analyzing the types of glycans attached to therapeutic glycoproteins such as monoclonal antibodies, and the amount of each type of glycan, has become an important quality control measurement in the production of such glycoproteins and in confirming that they will have the desired pharmacological activity.

Determining the types of carbohydrates present in a sample is typically conducted by labeling the carbohydrates and then analyzing the labeled carbohydrates using suitable instrumentation. N-glycans can be analyzed by releasing them from glycoproteins with enzymes such as PNGase F, labeling them, and then detecting the presence of the labeled compound, for example, by detecting their fluorescence. The glycans are released by the enzyme in the form of glycosylamines, which can then be labeled with amine-reactive dyes, such as INSTANTPC® (ProZyme, Inc.) and RAPIFLUOR-MS® (Waters Corp.), that quickly react with the amine moiety on the glycosylamines. The dyes react, however, not only with the glycosylamines, but also with any other amine groups in the solution. For example, buffers such as "TBE" (tris/borate/EDTA) and "TAE" (tris/acetic acid/EDTA) contain Tris(tris (hydroxymethyl) aminomethane), which bears a primary amine. When the glycosylamines of interest in a solution containing amine groups are labeled with an amine-reactive dye, the other amines in the solution can compete with the target glycosylamines for labeling by the amine-reactive dye, reducing the amount of dye available to label the glycosylamines of interest.

As noted in the Background section, therapeutic glycoproteins are expensive and some are available only in very small quantities. The quantities of glycosylamines released from a sample of such a glycoprotein are themselves correspondingly small, and may be on the order of picograms, while the amount of free amine in a Tris buffer or other solution containing the glycosylamines may be orders of magnitude higher. The excess of amines from the buffer or other source compared to the glycans of interest can therefore sharply reduce the sensitivity of the assay by outcompeting the glycosylamines for the amine-reactive dye. Thus, it can be difficult to detect the presence of small amounts of glycans present on glycoproteins in buffers that contain Tris or free amines from other sources amid the signal from the labeled amines in the buffer or present on other amine-containing compounds. Unfortunately, considerations such as stability, solubility, pH, or cost, may dictate that amine-containing formulants be used to permit shipping or storing the glycoproteins of interest.

Surprisingly, the present invention solves this problem, and allows sensitive detection of glycans (or, as they are released from glycoproteins by enzymatic digestion, glycosylamines) present in a sample, even when the sample is in a solution that contains amine-containing formulants, such as a Tris-containing buffer or other source of free amines.

In current protocols, N-glycans present on a glycoprotein are analyzed by denaturing the glycoprotein in an aqueous solution, which typically contains reductants, other denaturants, and buffer salts. The denaturing usually involves heating the aqueous solution comprising the glycoprotein to an elevated temperature, often around 95° C., and then cooling the solution. The glycoprotein is then typically deglycosylated by incubating it in an aqueous solution with a deglycosylation enzyme of choice, such as PNGase F. The resulting aqueous solution comprises not only the aqueous solution itself, in which the enzymatic digestion was performed, but also (i) the fully or partially aglycosylated protein remaining after N-glycans have been released as glycosylamines by action of the enzyme, (ii) any glycosylamines released by the enzymatic digestion, (iii) the deglycosylation enzyme, (iv) buffer salts, (v) reductants, and (vi) any other denaturants used in the denaturation step. In some embodiments, the glycoprotein may originally have been in a biological sample, in which case the solution may further contain lipids, additional proteins, salts, and other metabolites. These parts of the current workflow are shown schematically in FIG. 1 as items 1-3.

For convenience of reference, the production of the aqueous solution containing the glycosylamines following the denaturation and partial or complete deglycosylation of the glycoprotein will sometimes be referred to herein as "obtaining an aqueous solution containing the glycosylamines," and the solution itself will sometimes be referred to herein as the "starting glycosylamine solution." In current protocols, the amine-reactive dye is typically added to the starting glycosylamine solution to label the glycosylamines contained in the starting glycosylamine solution, and the labeled glycosylamines are then subjected to clean-up procedures to separate them from the other molecular species in the solution so that the labeled glycosylamine can be analyzed. The amine-reactive dye is in an organic solvent that is compatible with the starting glycosylamine solution and the starting glycosylamine solution does not need to be dried down before addition of the dye.

In embodiments of the inventive methods, the denaturation and deglycosylation steps proceed as usual. Once the N-glycans have been released from the glycoprotein as glycosylamines into the starting glycosylamine solution, however, the workflow changes. As illustrated in FIG. 1, item 4, an organic solvent is added to the starting glycosylamines solution, in an amount sufficient to change what started as an aqueous solution to a solution that is about 80% up to 95% organic solvent (and correspondingly about 20% down to 5% aqueous solution, with "about" in this context meaning±1%). For convenience of reference, the resulting solution, which is now about 80% to 95% organic solvent solution, may be referred to as the "organic solvent mixture." The practitioner can then immobilize the glycosylamines in the organic solvent mixture on a porous solid support, as shown schematically in FIG. 1, item 5. Without wishing to be bound by theory, glycosylamines in organic solvent solutions of the stated concentrations are believed to be retained on a hydrophilic porous solid support or a hydrophilic surface of a porous solid support by polar interactions between the glycosylamines and the support. The other components in the organic solvent mixture will generally remain in solution, pass through the porous solid support, and can be removed from the container holding the porous solid support. This results in the removal of most if not all of any amines in the starting glycosylamines solution available to react with the amine-reactive dye (other than those on the immobilized glycosylamines), and in the sharp reduction of the amount of any other free amines present.

Once the glycosylamines have been immobilized on the solid support, they can optionally be washed with an organic solution of about 80-95% organic solvent, preferably about 80% to about 90% organic solvent, to remove any amines not immobilized on the porous solid support, as shown in FIG. 1, item 6 and then can either (a) be labeled with the amine-reactive dye while on the solid support, as depicted in FIG. 1, item 7, optionally washed with a solution of about 80-95% organic solvent, preferably about 80% to about 90% organic solvent, to remove excess dye (FIG. 1, item 8), and then eluted by an aqueous solution so they can be provided to an analytical means, as depicted in FIG. 1, item 9, or, (b) be eluted from the solid support with an aqueous solution into a fresh container, labeled with the amine-reactive dye in the fresh container, and then provided to an analytical means (embodiment (b) is not shown on FIG. 1). With respect to labeling on the solid support (embodiment (a), above), amine-reactive dye is expensive and the practitioner typically uses only enough to saturate the porous solid support with dye. As the dye is typically in an organic solution, it will not elute glycosylamines from the support. As noted, following the labeling, the labeled glycosylamines can be eluted from the support with an aqueous solution and provided to an analytical means.

As noted, the labeled glycosylamines can be provided to standard analytical procedures to determine the type and quantities of N-glycans that were present on the glycoprotein or glycopeptide from which the glycosylamines were released. Typically, the labeled glycosylamines are separated by liquid chromatography (such as high-performance liquid chromatography (HPLC), ultra high-performance liquid chromatography, or, hydrophilic interaction liquid chromatography ("HILIC")), capillary electrophoresis, or microfluidic separation, and then analyzed by providing the separated, labeled glycosylamines to analytical means, such as to a fluorescence detector or a mass spectrometer. In some embodiments, the separated, labeled glycosylamines are provided first to a fluorescence detector and then to a mass spectrometer. Other analytical procedures and devices known in the art can, of course, also be used.

The inventive workflows add one or more steps to the workflow compared to current protocols, and the use of amounts of an additional reagent, the organic solvent used to create an organic solvent mixture of the desired percentage of organic solvent to the starting glycosylamine solution. The goal in modifying methods is usually to reduce the number of steps and to reduce the number and amount of reagents used, to simplify the workflow and to reduce costs. Counterintuitively, however, in this case, it is worth adding additional steps and reagents. The problem of reducing the impact of free amines in competing with glycosylamines for amine-reactive dye has not been well addressed by current methods, which rely either on avoiding the use of solutions that contain free amines or by buffer exchange, a tedious and not always effective method, which cannot be automated.

As set forth in the Examples, a study underlying the present invention was conducted in which an exemplar glycoprotein was denatured, deglycosylated, and then divided into four samples. Tris buffer was added to two of the samples to reach a concentration of 750 mM Tris, while an equal amount of water was added to the other two samples so that the sample volume of the four samples was the same. One sample to which Tris had been added and one sample to which water had been added were then labeled in solution with the amine-reactive dye INSTANTPC™ ((2-(diethylamino) ethyl 4-[(2,5-dioxopyrrolidin-1-yl)oxycarbonylamino))benzoate)) following the conventional workflow, and analyzed by fluorescence. An organic solvent, acetonitrile, was added to the other two samples (one to which Tris had been added and one to which water had been added) to create an organic solvent mixture of 85% organic solvent/15% aqueous solution, and each sample was immobilized on a solid support used for HILIC separations of carbohydrates or for solid phase extraction of carbohydrates. The solid support was washed twice with an 85% organic solvent/15% aqueous solution to remove free amine while keeping the glycans immobilized. The immobilized glycosylamines were then labeled with INSTANTPC™ eluted from the solid support, and analyzed by fluorescence.

Figure 2:
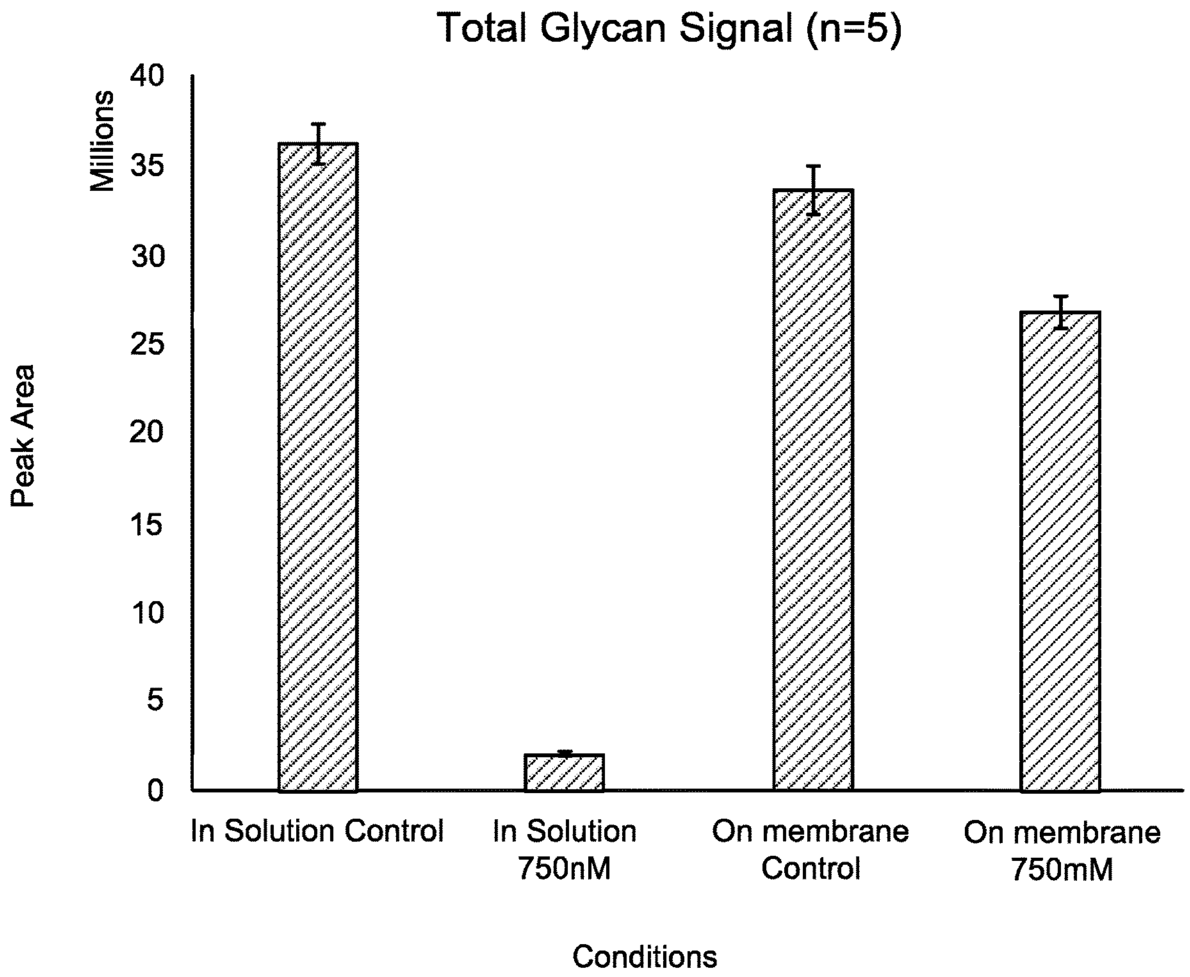
FIG. 2. The left side of FIG. 2 presents a bar graph showing the results of labeling glycosylamines that have been labeled by the amine-reactive dye INSTANTPC™ while the glycosylamines are either in solution (first two bars from the left) or while immobilized on a porous solid support (third and fourth bars from the left) and either in the presence of 750 mM Tris buffer (second and fourth bars from the left) or the absence of Tris buffer (first and third bars from the left). The right side of FIG. 2 sets forth the procedure used to conduct the study whose results are shown on the graft on the left side of the Figure.

FIG. 2 is a graph showing the results of the fluorescence analysis of the glycosylamines labeled in the presence or absence of Tris buffer, containing amines competing with the glycosylamines for the amine-reactive dye. The two left-hand columns show the results for the samples labeled in solution. The first column shows the result for the sample to which water had been added and then labeled in solution: it has a peak area of about 36. The second column shows the result for the sample to which Tris had been added and then that was then labeled in solution: it has a peak area of about 2, or a signal approximately 18 times lower than the sample labeled without the presence of Tris. Stated another way, the peak area of the sample labeled in the presence of Tris was 5.55% of the the peak area of the sample labeled in its absence. The results demonstrate the difficulty of labeling glycosylamines in the presence of amines in the solution competing for label.

Referring to FIG. 2, the two right-hand columns show the results for the samples labeled while immobilized on the porous solid support. The second column from the right-hand side shows the result for the sample to which water had been added, immobilized on the porous solid support, and then labeled while immobilized on the support: it has a peak area of about 33, and thus the signal is a bit lower than that of the corresponding sample labeled in solution. The column on the right-hand side of the graph shows the result for the sample to which Tris had been added, immobilized on the porous solid support, washed to remove free amines, and then labeled: it has a peak area of about 27, or a signal approximately 81% that of the sample labeled in the absence of Tris, a dramatic improvement from that of the corresponding samples labeled in solution. Further, the peak area of the Tris-containing sample that was immobilized, washed, and then labeled, was 27, more than an order of magnitude greater than the sample labeled by the same amine-reactive dye in solution in the presence of Tris.

Thus, as shown on FIG. 2, the inventive methods dramatically improve the sensitivity of labeling and the ability to subsequently detect labeled glycosylamines that are in an aqueous solution that contains amines that can compete for labeling with an amine-reactive dye. While this will be the case for samples that are in a Tris-based buffer, or other buffer or solution known to contain amines available to react with the amine-reactive dye, some samples may have unknown amounts of such amines present. Further, the practitioner may wish to adopt a single workflow for all glycosylamines analyses that will still be sensitive enough to give good results whether or not samples come in that have amines are present in the buffer or other solution. Accordingly, embodiments of the inventive methods are expected to become a common workflow, particularly where samples to be analyzed may be uncharacterized (e.g., biological samples), may contain Tris- or other amine-containing buffers, or may have other sources of free amines that could interfere with labeling.

Certain aspects of various embodiments of the inventive methods are now discussed to provide further explanation and guidance Organic Solvents Organic solvents are used in embodiments of the inventive methods to reduce the concentration of the aqueous starting glycosylamine solution to a point at which glycosylamines in the sample will be retained on the porous solid support, allowing other compounds in the starting glycosylamine solution to be removed by, for example, washing the porous solid support with the resulting organic solvent mixture. In some embodiments, the organic solvent is acetonitrile, the use of which is particularly preferred. Acetonitrile is both hydrophobic and aprotic. It is anticipated that other organic solvents can be used in embodiments of the inventive methods, and organic solvents that are both hydrophobic and aprotic are preferred. A variety of other organic solvents are believed suitable for use in embodiments of the present invention, including absolute ethanol, absolute methanol, isopropanol, butanol, toluene, ethyl acetate, acetone, tetrahydrofuran, diethyl ether, dichloromethane, chloroform, tert-buthyl-methyl ether, benzene, carbon tetrachloride, isooctane, and hexane. Mixtures of two or more organic solvents, such as those mentioned, may also be used.

Dimethyl sulfoxide ("DMSO") and dimethylformamide ("DMF") are less preferred to serve as the primary organic solvent or as a major constituent of a mixture of organic solvents for use in embodiments of the inventive methods. It is believed DMSO or DMF can be mixed with one of the organic solvents mentioned in the preceding paragraph, or with a mixture of organic solvents mentioned above, in relatively modest amounts (such as 0.1% to 2%), without affecting the ability of the solid support to retain the glycosylamines in the presence of the organic solvent or mixture of organic solvents.

As glycans and other carbohydrates are hydrophilic, they will tend to be retained on hydrophilic surfaces when they are in solutions that are about 80%-95% organic solvent. In some preferred embodiments, the concentration of organic solvent is about 85%, with "about" in this context meaning ±2%.

Persons of skill will appreciate that no one organic solvent can be used in all situations, on all solid supports that might be suitable for use in embodiments of the inventive methods. Further, persons of skill in the art of labeling glycans released from glycoproteins are aware that it is common to have to test combinations of reagents to determine if the combination is useful in releasing, labeling, and analyzing the glycans present on many glycoproteins and that such testing is considered routine in the art. Practitioners can readily test any particular organic solvent for its suitability with respect to any particular sample containing a glycan the practitioner wishes to label by any particular amine-reactive dye, and any particular solid support on which the practitioner wishes to retain the glycosylamines for labeling, by adding an excess of the organic solvent being tested to a starting glycosylamine solution sample containing a known amount of a selected glycosylamine (the "test glycosylamine"), contacting the solvent/solution mixture to the solid support of choice (whether one already known to be useful in protocols for labeling glycosylamines or a porous solid support being tested for its utility for this purpose), labeling the glycosylamines with the amine-reactive dye of choice, eluting the glycosylamines from the solid support with an aqueous buffer, and subjecting the eluted solution to analysis to determine if the test glycosylamine has been labeled and, if so, whether it is present in the amount expected. If labeled test glycosylamine is not identified in the analyzed eluant in the amount expected, this indicates that the particular combination of organic solvent, of label, and of solid support, was not suitable for labeling the test glycosylamine with that label.

Adding Organic Solvent to the Starting Glycosylamine Solution

In the inventive methods, the starting glycosylamine solution containing the glycosylamines of interest (and which may also contain proteins, denaturants, salts, enzymes, or other compounds) is in an initial container. The starting glycosylamine solution sample is then mixed with organic solvent to create an organic solvent mixture of the chosen concentration of organic solvent (i.e., about 80% to 95%, about 80 to 90%, 85%±3%, preferably 85%±2%, with "about" meaning ±1%) when the organic solvent mixture in placed into contact with the porous solid support. Persons of skill will appreciate that there are a number of ways to accomplish this. For example, organic solvent in amounts to create the desired concentration of organic solvent in the organic solvent mixture can be added to the container initially holding the starting aqueous solution sample. Or, the starting glycosylamine solution sample can be transferred to a larger container and mixed with organic solvent to create a mixture having the desired concentration of organic solvent before adding it to a container with the porous solid support. Alternatively, a quantity of organic solvent can be present in a container holding the porous solid support so that, when the starting glycosylamine solution is added to the container, the mixture of the organic solvent and starting glycosylamine solution creates a mixture with the desired concentration of organic solvent (in these embodiments, any exit from the container is preferably capped or closed so that the starting glycosylamine solution mixes with the organic solvent to create a mixture of the desired concentration, rather than flowing out). Finally, one can start adding the desired amount of organic solvent to the container holding the porous solid support and start adding the starting glycosylamine solution to the container slowly enough so that the mixture of the organic solvent and starting glycosylamine solution in the container at the porous solid support is at the desired concentration of organic solvent to starting glycosylamine solution.

As described in the Examples, in studies underlying the present disclosure, organic solvent was added to a starting glycosylamine solution in an amount that created an organic solvent mixture that was 85% organic solvent and 15% aqueous solution.

For convenience of reference, the container holding the porous solid support will sometimes be referred to herein as the "reaction container." (In microfluidics apparatuses, the starting glycosylamine solution sample is not transferred to a separate container holding the porous solid support, but rather from a first section of a channel, tubing, or the like to a second section of channel, tubing, or the like, which second section contains the porous solid support. The phrase "reaction chamber" is sometimes used herein to denote the section of a microfluidics device configured for use in embodiments of the inventive methods. For convenience of reference, the discussion below will be generally discussed with relation to embodiments in which the starting glycosylamine solution transferred to a reaction container, but will be understood to also relate to microfluidics applications in which the starting glycosylamine solution is transferred to a section comprising a space large enough to hold the mixture of organic solvent and starting glycosylamine solution sample and the porous solid support, unless otherwise stated or required by context.) The reaction container has a first opening, usually at the top, through which solutions and reagents may be introduced, a body, typically cylindrical, and containing the porous solid support, and a second opening, usually disposed at the bottom of the container, which is typically opposite the first opening. The second opening may be closable to prevent solutions from exiting the reaction container until desired. The body of the container has a lumen which has a cross section (circular, in the case of a cylindrical body) which has an area defined by the interior dimensions of the body. The porous solid support is typically positioned in the reaction container, filling the cross sectional area of the reaction chamber so that the organic solvent mixture containing the glycosylamines to be labeled has to go through pores or openings in the porous solid support to reach the second opening.

In some typical embodiments, the container can be open at the end at which the container is designed to have liquids exit the container (typically the bottom, if the container is designed so that liquids move vertically from top to bottom, or, horizontally, as might be the case in some microfluidic applications, in which a microfluidic tube might be designed to have fluids introduced from one side and to exit out another, out an opening other that the one from which they are introduced). If desired, however, the container can have a manual or automated means of sealing the exit opening so that the reagents are retained until in the container during steps requiring their presence, while allowing opening the exit opening to permit them to drain or to be eluted from the container when desired. For example, the bottom can have a flap, cap, or other covering that, when closed over the opening, allows fluids to be retained in the container and which, when open, allows fluids to exit the container. In microfluidic applications, in which the labeling takes place in a reaction chamber which may be vertically disposed or horizontally disposed, there may be, for example, one or more valves between the reaction chamber and the channel or other path through which the practitioner wishes the reactants to proceed, with a valve separating the reaction chamber from a particular channel being opened to permit solutions and solvents to be eluted from the reaction chamber along the desired path.

Materials for the Solid Support

The material selected for the porous solid support either is in a configuration, such as being woven to permit the organic solvent mixture to contact a large surface area of the material, or has a plurality of pores or opening that allow the organic solvent mixture to contact a large surface area of the material. In some embodiments, the porous solid support is made of a hydrophilic material that preferentially retains glycosylamines over proteins, buffer salts, reductants, or other reagents known to be present in a particular mixture from which the carbohydrates are to be separated.

Persons of skill will appreciate that the glycosylamines can be retained on the porous solid support in a matter of seconds, but it is not desirable for the glycosylamines to flow past the solid support so quickly (for example, less than 1 second) that retention does not have time to occur, nor so slowly (for example, more than 15 minutes) that unnecessary time is added to the protocol. Flow speeds through the porous solid support therefore should be slow enough for the glycosylamines to have the opportunity to be retained on the porous solid support, but fast enough to avoid delays that add unnecessary time to the workflow. Persons of skill are familiar with selecting materials, such as for cartridges used in solid phase extraction protocols, with pore sizes and other characteristics resulting in a desired flow speed, as well as with the use of various procedures, such as positive pressure, centrifugation, or use of a vacuum manifold, for increasing the flow rate of liquids over or through a solid support. It is expected that practitioners are well familiar with extracting glycosylamines from a sample using solid phase extraction procedures by choice of material, pore sizes, and flow rates used in the extraction and that this familiarity provides ample guidance regarding choices of material for the porous solid support, for the pore size, and for flow rates for use in flowing the solvent/solution mixture through the porous solid support in various embodiments of the inventive methods.

In some embodiments, the porous solid support is made of a material that is used for solid phase extraction ("SPE") of carbohydrates or for hydrophilic interaction liquid chromatography ("HILIC") separations of carbohydrates. It is contemplated that materials used in HILIC separations of carbohydrates and in SPE extraction of carbohydrates are generally suitable for use in the porous solid support. SPE is widely used in the art and there are numerous teachings about materials suitable for use in SPE and how to conduct it, as exemplified by Thurman and Mills, Solid-Phase Extraction: Principles and Practice, John Wiley & Sons Inc. (New York, NY, 1998), N. Simpson, Solid-Phase Extraction: Principles, Techniques, and Applications, Marcel Dekker Inc. (New York, NY, 2000), and Waters Corp., Beginner's guide to SPE: Solid-Phase Extraction, John Wiley & Sons Inc. (New York, NY, 2014). Accordingly, it is expected that persons of skill can readily select materials appropriate for use as the porous solid support.

Examples of hydrophilic materials that can be readily configured to serve as a porous solid support include: (a) cellulose, (b) glass fibers, (c) alumina, (d) aminopropyl, (e) aspartamide, (f) cyclodextrin, (g) triazole, (h) diethylaminoethyl, (i) resins typically used in HILIC separations of carbohydrates, (j) silica that has been modified with diol, cyanopropyl, ethylenediamine-N-propyl, or amide (carbamoyl) groups, or (k) combinations of two or more of these materials. In some embodiments, the porous solid support can be graphitized carbon, which binds glycosylamines, but its use is less preferred because, among other things, it can be saturated with the surfactant usually used in denaturing the glycoprotein or glycopeptide.

In some preferred embodiments, the porous solid support is composed of silica beads or particles that are covalently bonded with carbamoyl groups. In some preferred embodiments, the silica beads or particles that are covalently bonded with carbamoyl groups are Amide-80. In some preferred embodiments, the Amide-80 beads or particles are 3-60 microns in size, more preferably 5-50 microns in size and still more preferably about 30 microns in size, with "about" here meaning ±2 microns. As used herein, the terms "functionalized," "derivatized," and "modified" (in the context of a material that might serve as a porous solid support) are equivalent and mean that the surface of the material forming the body of the solid support is covalently bonded to molecules of one of the functional groups (e.g., aminopropyl, diol, carbamoyl) listed or, in some embodiments, to molecules of two or more of these functional groups (e.g., both diol molecules and carbamoyl molecules are covalently attached to the surface of the material of the porous solid support).

As noted, in some embodiments, the porous solid support can be made of glass. Preferably, the glass is in a form that has a high amount of surface area to facilitate retention of glycosylamines in the solvent/solution mixture and preferably is in a form through which the mixture can be flowed to facilitate such capture. For example, the glass can have a plurality of small holes allowing fluids to filter through it or be in form of beads or particles. In some preferred embodiments, the glass is in the form of glass fibers. In some embodiments, the glass fibers can be loose. In some embodiments, the glass fibers can be woven. In embodiments in which the glass fibers are loose, the fibers will typically be used in conjunction with an underlying structural support that holds the fibers in the container while solvents, solutions, and unwanted reagents are flowing through. In these embodiments, the structural support is disposed between the glass fibers and the opening through which the solvents, solutions and unwanted components exit from the container. Or, the container can be configured with an exit that is small enough to hold the fibers in place while allowing solutions to flow out.

In some embodiments, the porous solid support can be made of a form of aminopropyl. Various forms of aminopropyl are known in the art to be useful for separating carbohydrates and several are commercially available. For example, aminopropyl AP (NH2) HPLC columns for separating carbohydrates are available from Separation Methods Technologies, Inc. (Newark, DE). APHERA™ NH2 HPLC columns are sold by Sigma-Aldrich Co. (St. Louis, MO) Aminopropyl silanes are used in the art for HILIC separation of sugars. It is expected that persons of skill are familiar with the various ways in which aminopropyl is used for separating carbohydrates in procedures such as HPLC and HILIC and can select suitable forms of aminopropyl for binding glycosylamines in embodiments of the inventive methods in which an aminopropyl is to be employed.

In some embodiments, the porous solid support can be made of cellulose. Cellulose can be used in sheets, but it is commonly used in solid phase extraction as a microcrystalline powder and that form is preferred as it provides a larger surface area for binding the glycosylamines. As practitioners will appreciate, use of solid phase supports that are in the form of powders, nanoparticles, or other small particles will typically be used in conjunction with a filter or other structure that allows solvents, solutions, and unwanted reagents to flow through upon elution while the powder or nanoparticle or other small particles are retained in the container. In these embodiments, the filter or other structure is disposed between the powder, nanoparticles, or other small particles and the opening through which the solvents, solutions and unwanted components exit from the container.

In some embodiments, the porous solid support can be magnetic beads functionalized with diol, cyanopropyl, ethylenediamine-N-propyl, or amide (carbamoyl) groups.

It is further contemplated that the material used for the porous solid support will release the retained glycosylamines upon being washed with an aqueous solution, such as phosphate buffered saline (for clarity, it is noted that the aqueous solution that elutes the glycosylamines from the porous solid support in this step differs from the organic solvent/aqueous solution mixture used to wash excess label off the porous solid support, as depicted schematically in the optional wash shown in FIG. 1, items 6 and 9, as the aqueous solution does not contain the about 80%-95% concentration of organic solvent of that wash. Typically, 20% or less of the solution used to elute the retained glycosylamines from the porous solid support is an organic solvent, with at least 80%, and preferably more, being an aqueous solution.)

Less commonly, in some embodiments, the porous solid support may be made of a non-hydrophilic material, but be coated on its surface with a hydrophilic material. Since glycosylamines are retained on solid supports by interactions with the surface, not by interacting with any non-hydrophilic material underlying the hydrophilic material on the surface, it is expected that the glycosylamines will interact with the solid support as they would if it were made of a hydrophilic material. Accordingly, embodiments of the inventive methods in which a porous solid support is made of a non-hydrophilic material, but is coated on its surface with a hydrophilic material, are treated as if the porous solid support was made a hydrophilic material.

Without wishing to be bound by theory, it is believed that in an organic solvent mixture with concentrations of organic solvent from about 80% to 95% (with about here meaning ±1%) and the use of a porous solid support of a hydrophilic material, the glycosylamines in the sample are retained on the porous solid support by hydrophilic interactions. Without wishing to be bound by theory, it is believed that, at concentrations of organic solvent over 95% and the use of a porous solid support, the glycosylamines sample will precipitate or aggregate, and can be captured and retained on the solid support by simple filtration through pores or openings in the porous solid support regardless of whether the material of the porous solid support is hydrophilic or non-hydrophilic. For example, if the practitioner chooses to raise the concentration of organic solvent above 95%, for example, to 99% or higher, diluting the aqueous component to the point that the glycosylamines are in what is almost neat organic solvent, non-hydrophilic materials can be used for the porous solid support. This allows the practitioner to use materials, such as polyethylene, nylon, polyvinylidene fluoride, or polypropylene, that are less expensive and easy in which to create pores or openings of a desired size (e.g., 10 microns or less) for the porous solid support. As with the hydrophilic materials discussed above, the non-hydrophilic material chosen for use as the porous solid support should not be one that contains or is derivatized with chemical groups expected to react with proteins or other compounds that are expected to be in the organic solvent mixture. Without wishing to be bound by theory, it is believed that, in concentrations of organic solvent above 95%, glycosylamines aggregate or precipitate out of the starting glycosylamine solution sample and can captured and retained on the porous solid support by filtering them through pores or openings of 10 microns or less in the porous solid support. While the use of solutions with a concentration of organic solvent above 95% therefore permits the use of a broader range of materials for the porous solid support, such as polyethylene, it also reduces the amount of aqueous solution present to help wash off from the porous solid support non-wanted reagents that may contain free amines and thus compete with the glycosylamines for labeling with the amine-reactive dye. It is therefore believed that embodiments in which the organic solvent mixture has a concentration of organic solvent from about 80% to 95% (with about here meaning ±1%) and in which the porous solid support is made of or has a surface of a hydrophilic material are generally preferred in embodiments of the inventive methods.

Form of the Porous Solid Support

The term "solid support" means that the support has a solid surface, but it is not necessary that the solid support be made of a single piece of the material from which it is made. The "solid support" can, for example, be composed of a plurality of derivatized silica beads or particles which when grouped together and disposed across the interior of a container provide a hydrophilic surface on which glycosylamines can be retained. If the solid support is made of beads or particles, the beads or particles may be compacted or retained in, for example, a plastic retainer, to retain the beads or particles at the desired position in the container. In such embodiments, the plastic retainer may be composed of a plastic ring sized to just fit across the lumen of the container, with strands of plastic cross hatched from the ring like the strings of a tennis racket across the interior of the container, with holes between the cross hatched strands creating spaces smaller than the diameter of the beads or particles, thereby keeping the beads or particles in place while allowing liquids to flow through. Similarly, the solid support can be made of glass fibers which can be disposed over and across one another to provide surfaces on which glycosylamines can be retained. If needed, the glass fibers can be retaining in place by a plastic retainer like the one described above. In some embodiments, the beads, particles, glass fibers, or the like can be packed into a bed at the bottom of the container. Beads and other particles can be retained by, for example, narrowing the walls of the container to a diameter below the diameter of the beads or particles, or by positioning a suitable retainer with cross hatched pieces which leave holes or openings too small for the beads or particles to pass through, but which allow fluids to be eluted from the container.

In some embodiments, the hydrophilic material is shaped into a membrane or a monolith which is rigid as well as porous. The membrane or monolith can then be shaped into a shape fitting precisely into the lumen of the container and filling the cross section of the lumen at the desired position. Alternatively, the membrane or monolith can be shaped into a shape slightly smaller than the lumen of the container, and be held in place by, for example, a lip or ledge around the interior of the container, or by two or more projections from the interior of the container disposed to position the membrane or monolith at the desired position.

Whether the porous solid support is of beads, particles, a membrane, or a monolith, it is positioned at the desired point in the container across the entire cross section of the container's lumen so that solutions or solvents in the container must pass through the porous solid support before exiting. If the container narrows from a cylindrical section to a conical section as, for example, in an Eppendorf tube, the beads, particles, membrane or monolith can, for example, be sized to completely cover the area of the bottom of the cylindrical section and be retained in position by the narrowing below of the wall of the container to form the conical section (although, unlike a normal Eppendorf tube, the containers used in embodiments of the inventive methods preferably have a hole at the bottom to allow fluids to be eluted from the container. Similarly, if the container is the cylindrical portion of a well of a multiwell plate, and the well has a nozzle at the bottom with an opening allowing solutions to exit the well when desired, the membrane or monolith can be sized to completely cover the area of the bottom of the cylindrical section of the well and be retained in position by the narrowing of the wall of the well to form the nozzle section below the membrane or monolith, while beads or particles can be retained by narrowing the sides of the well to be narrower than the diameter of the beads or particles, while still allowing fluids to exit. In embodiments in which hydrophilic materials are used for the porous solid support, and the glycosylamines are not of monosaccharides or very small, the pore or opening size can be larger than in the embodiments discussed below, so long as the pores or openings force the glycosylamines to come into contact the hydrophilic material as the organic solvent mixture flows through the porous solid support. The glycosylamines will tend to interact with, and be retained on, the hydrophilic material of the solid support when in an organic solvent that is in a concentration of 80% or more organic solvent to 20% or less aqueous solution.

As used herein, the terms "porous" and "permeable" used in describing a solid support are intended to convey that the solid support allows solvents and solutions to filter gradually through it. All solid supports described in this disclosure are porous solid supports unless otherwise specified or required by context. It should be noted that the porous solid supports may in some embodiments rest on or be held in place by, for example, fittings, narrowing of the container walls, or internal structures of the container in which they are disposed. Such fittings, narrowings, or internal structures are solid and may retain or support the porous solid supports, but they are need not be made of the same material as that of the reaction container and are not intended to be considered as being a porous solid support as that phrase is used in this disclosure.

The form of the porous solid support can vary according to the practitioner's choice, so long as it is fashioned to require the organic solvent mixture containing the glycosylamines to be labeled to go through it. For example, the porous solid support can be a monolith, a filter or membrane across the lumen of a tube, such as that of a microfluidic device, or can be glass fibers or a resin filling some or all of the interior of a solid phase extraction ("SPE") cartridge. In some embodiments, the material for the solid support can be in the form of beads or particles, which can be held in place within the reaction container by, for example, a frame of plastic with cross hatching smaller than the diameter of the beads or particles, positioned under the beads or particles within the lumen of the container. If the porous solid support is a resin, it can, for example, be positioned in a container having a conical end, tapering to a diameter that will let liquid through but not the resin.

The organic solvent mixture is typically flowed through the porous solid support. In some embodiments, the organic solvent mixture containing the glycosylamines may be drawn through the porous solid support by having a vacuum applied downstream of the porous solid support or, particularly in microfluidic devices, may be pushed through by pressure from upstream of the porous solid support. It should be noted that persons of skill have used various solid phase materials, such as solid phase extraction cartridges for years to capture glycans for "clean up" steps of many protocols, and are thus presumed to be familiar with the various shapes, configurations, and types of materials suitable for use in capturing glycosylamines present in an organic solvent mixture while allowing unwanted components in the mixture to be washed away.

Eluting the Glycosylamines from the Porous Solid Support

Glycosylamines retained on the porous solid support in the presence of the organic solvent mixture, which is about 80-95% organic solvent, can be eluted from the porous solid support with an aqueous solution. Up to 20% of the solution used to elute the glycosylamines from the solid support can be an organic solvent, but it is at least 80% aqueous solution, with higher concentrations of aqueous solution being preferred. It should be noted that the "aqueous solution" can be water, but is preferably a buffer solution, such as HEPES (2-[4-(2-hydroxyethyl)piperazin-1-yl]ethanesulfonic acid) buffer, phosphate buffered saline, or ammonium formate buffer. The presence of the salts in the buffer solutions increases the polarity of the aqueous solution, enhancing the release of the glycosylamines from the solid support during elution. The buffers help maintain the glycosylamines in a pH controlled solution, increasing their stability.

The eluted, labeled glycosylamines are then collected and available to be provided to analytical instruments for analysis. For example, the labeled glycosylamines can be separated by high-performance liquid chromatography, capillary electrophoresis, microfluidic separation, or hydrophilic interaction liquid chromatography ("HILIC"). Labeled glycosylamines may then be analyzed by detecting their fluorescence and measuring the intensity of that fluorescence, by mass spectrometry, or a combination of detecting the fluorescence intensity and mass spectrometry Containers Holding Solid Supports As noted above, in typical embodiments, the glycosylamines to be labeled are initially in an aqueous solution, which is then diluted by adding to the solution larger amounts of an organic solvent. Conveniently, the resulting organic solvent mixture containing the glycosylamines is placed into a second container designed for this purpose. In typical embodiments, the container has a body having a length and two ends. In some embodiments, the two ends are disposed opposite each other along the length of the body of the container. The ends are each independently open or may independently be openable to allow the introduction of solutions and reagents at the first end and the exit of solutions and reagents at the second end. In some embodiments, the container is cylindrical. In some embodiments, the container is cylindrical, but narrows to a nozzle at the second end to facilitate capture of eluted labeled glycosylamines for analysis when they are eluted. In some embodiments, the container may be similar to a standard Eppendorf tube, microfuge tube, or centrifuge tube, but with an opening at the bottom. Typically, such tubes have a first section that has an open or openable first end opening, a cylindrical body, connecting to a second section opposite the first end, which second section has a conical shape that narrows as it proceeds away from the cylindrical first part, until it reaches a second end. The second end can be open, but in some embodiments can be closable, allowing solutions in the container to incubate in the container when the bottom end is closed, but to allow solutions to flow out of the container when the second end is opened. For example the bottom end may be fitted with a cap or a removable cover to allow the user or an automated device to open the bottom end and allow a solution in the container to flow out. In other embodiments, the container can be generally cylindrical, conical, tetrahedral or cuboidal in shape. The containers may be shaped to be received into an apparatus designed to receive them, in which case they may be referred to as "cartridges."

In some embodiments, the second container is a well in a multi-well plate, and in preferred embodiments, each well of the multi-well plate is a container adapted for capturing and retaining glycosylamines Such wells typically have a cylindrical body narrowing to a bottom section comprising an opening to allow solutions to exit the well. The exit at the bottom of the well is preferably narrower than the diameter of the well and can be a nozzle that projects from the bottom of the well, particularly where it is desired to use the plate in a system for automated collection of samples.

Whether the second container is a tube, a cartridge, or a well, it has a porous solid support disposed between the top of the container and the exit. In a well comprising a nozzle, the first porous solid support is preferably disposed just above the nozzle. The porous solid support is a preferably a hydrophilic material, as discussed in previous sections. In embodiments in which the porous solid support is, for example, comprised of beads, such as derivatized silica beads, the exit can have a diameter smaller than the diameter of the beads, or the beads can be held in place by conventional means, such as by having one or more porous compression frits, or by having a plastic retainer under the beads that has inter cross members.

Solid phase extraction (SPE) cartridges and other devices containing hydrophilic polymers for retaining carbohydrates typically have a means for retaining the polymers within the devices. These means are typically selected to be non-reactive with the carbohydrates and other reagents to which they are expected to be exposed and to permit fluids, such as wash solutions, to exit the device through the intended egress, such as a nozzle. Any of these conventional means can be used or adapted to retain the porous solid support in the devices.

The reaction containers themselves are made from materials that are non-reactive with the reagents and solutions that will be used in them. Typically, the reaction containers are of plastic. Cartridges and containers for the SPE of carbohydrates are well known in the art and available from a number of vendors. The plastics or other materials used for SPE cartridges used to separate carbohydrates from other types of compounds, such as proteins, are generally suitable for use in the inventive methods.

Eluting Retained Glycosylamines from the Porous Solid Support

Once any excess label has been removed from the labeled glycosylamines retained on the porous solid support, the retained labeled glycosylamines are eluted from the porous solid support by washing the support with an aqueous solution. Aqueous solutions to which salts have been added are preferred. Combinations of solutions can also be used. The aqueous solution may comprise up to 20% organic solvent or be only of water or buffer solution. Any particular solution or combination can be readily tested for its suitability in eluting glycosylamines from a solid support made of any particular material by performing parallel assays.

Kits

In some embodiments, the invention provides kits for labeling glycosylamines released from a glycoprotein or glycopeptide by enzymatic digestion according to the methods discussed above. The kits contain reagents and materials for deglycosylating the glycoprotein or glycopeptide by enzymatic digestion, for creating an organic solvent mixture containing the resulting glycosylamines, for immobilizing the glycosylamines on a porous solid support, and then for labeling them with an amine-reactive dye.

The kit include a deglycosylation enzyme. In some embodiments, the enzyme is PNGase F. The kit comprises an aqueous solution, such as a buffer, suitable for incubating the glycoprotein or glycopeptide with the deglycosylation enzyme. In embodiments for denaturing the kits may further contain a detergent or denaturant.

The kit further includes an organic solvent, such as acetonitrile, absolute ethanol, absolute methanol, isopropanol, butanol, toluene, ethyl acetate, acetone, tetrahydrofuran, diethyl ether, dichloromethane, chloroform, tert-buthyl-methyl ether, benzene, carbon tetrachloride, isooctane, hexane, or a combination of any two or more of these. In some embodiments of the kits, the organic solvent is acetonitrile. The enzyme, solution, and solvent, and detergent or denaturant, if included, are conveniently provided in separate containers.

In some embodiments, the aqueous solution and the organic solvent are each provided in the kit in pre-measured amounts such that, when combined, they form a mixture of organic solvent and aqueous solution that is 80-95% organic solvent to 20-5% aqueous solution. In some embodiments, the pre-measured amounts are such that, when combined, they form a mixture of organic solvent and aqueous solution that is 80-90% organic solvent to 20-10% aqueous solution. In some embodiments, the pre-measured amounts are such that, when combined, they form a mixture of organic solvent and aqueous solution that is 85%±2% organic solvent to 15%±2% aqueous solution.

The kit further comprises a container having disposed within it a porous solid support. The porous solid support is disposed within the container in a position so that the mixture of organic solvent and aqueous solution containing the released glycosylamines goes through the porous solid support when the mixture is introduced to the porous solid support, for example, by pouring or pipetting the mixture over it. In some embodiments, the porous solid support is in the form of a membrane. In some embodiments, the porous solid support is a hydrophilic material. In some embodiments, the hydrophilic material is (a) cellulose, (b) glass fiber, (c) alumina, (d) silica, (e) a functionalized surface containing diol, aminopropyl, carbamoyl, cyanopropyl, ethylenediamine-N-propyl, (f) silica derivatized with diol, aminopropyl, or carbamoyl, (g) cellulose, (h) cyclodextrin, (i) aspartmamide, (j) triazole, (k) diethylaminoelthyl, (l) a resin used in solid phase extraction of carbohydrates, or, (m) a combination of two or more of these. In some embodiments, the porous solid support is made of silica and said silica is covalently bonded to one or more carbamoyl groups. In some embodiments, the silica is in the form of beads or particles. In some embodiments, the beads or particles are from 3-60 microns in size. In some embodiments, the beads or particles are about 30 microns in size. In some embodiments, the beads or particles covalently bonded to carbamoyl groups are Amide-80.

The kit further comprises an amine-reactive dye. In some embodiments, the dye is INSTANTPC™, ((2-(diethylamino) ethyl 4-[(2,5-dioxopyrrolidin-1-yl)oxycarbonylamino))benzoate)

EXAMPLES

Example 1

This Example sets forth abbreviations for some of the reagents used in exemplar workflows of labeling procedures performed using exemplar carbohydrates in some of the Examples below.

"SDS": sodium dodecyl sulfate

"Tris": tris(hydroxymethyl)aminomethane

"PNGase F mix": a 1:1 mix of PNGase F mg/mi) and 750 mM HEPES ((4-(2-hydroxyethyl)-1-piperazineethanesulfonic acid) pH 8.0 buffer.

Example 2

This Example sets forth an exemplar workflow for N-Glycan INSTANTPC™ labeling using an exemplar amide support.

N-Glycan Release and Preparation

Four samples of 10 μl of 4 mg/ml an exemplar glycoprotein, etanercept, were added to wells on a PCR plate. Two μl of SDS was added to each well and the PCR plate was incubated for 3 minutes at 90° C. to denature the glycoprotein. After cooling the samples to below 50° C., 2 μl of PNGase F mix was added to each well to cause enzymatic digestion of the glycoproteins and release the glycans from the glycoprotein as glycosylamines. The PCR plate was then incubated for 5 mins at 50° C. Ten μl of 1.5M Tris pH 8 buffer was then added to each of two samples to reach a final concentration of 750 mM Tris, while 10 μl of $H_2O$ was added to each of the other two samples, to keep the volume of the four samples the same. The volume of each sample was approximately 26 μl.

Labeling and Subsequent Analysis of Two Samples Maintained in Solution

One sample to which Tris buffer had been added and one sample to which only water had been added were each labeled by adding 15 μl of a labeling reaction mixture (INSTANTPC™ dye mixed with Dye solvent) to the aqueous solution, which also contained with the now-deglycosylated glycoprotein, SDS, PNGase F and any other reagents present in the buffer and PNGase F mix. Both samples were incubated at 50° C. for 3 minutes. Water was added to each sample to bring the volume up to 100 μl to bring the sample volume the same as the sample volume of the samples discussed in the next section. One μl of each sample was then injected for high performance liquid chromatography (HPLC) separation and subsequent analysis by fluorescence of the labeled glycosylamines.

Immobilization of Two Samples and their Subsequent Labeling

The other two samples, one to which Tris buffer had been added and one sample to which only water had been added, each with a volume of approximately 26 were mixed with 174 μl of an organic solvent, acetonitrile, to form a solution of approximately 85% organic solvent and 15% aqueous solution. The resulting mixture was loaded on a "MonoSpin" Amide solid phase extraction ("SPE") centrifuge column (GL Sciences, Inc., USA, Torrance, CA), allowing glycosylamines in the mixture to be immobilized on the solid support in the column, while other components in the acetonitrile/water solution flowed through. The solid support was then washed once with a solution of 85% acetonitrile/15% water.

Each sample was then labeled by adding 15 μl of a labeling reaction mixture (INSTANTPC™ dye mixed with dye solvent) to the solid support to label any glycosylamines immobilized on the solid support. Both samples were incubated at 50° C. for 3 minutes. The now-labeled glycosylamines were then eluted by washing the solid support with 100 μl of an aqueous solution. Following the elution, 1 μl of each sample was injected for separation by high performance liquid chromatography and analysis of fluorescence of the labeled glycosylamines.

Example 3

This Example reports the results of the study set forth in Example 2.

The results are depicted in graph form in FIG. 2. The two columns on the left of the graph show the fluorescence of the samples that were labeled in solution. The control (the sample to which only water was added to the deglycosylation mixture) shows a peak area of over 35 million units, while the sample containing Tris buffer shows a peak area of about 2 million, reflecting the difficulty in detecting glycosylamines when Tris buffer or another source of amines that can react with the amine-reactive dye is present in the sample. The two columns on the right of the graph show the fluorescence of the samples that were placed into a 85% organic solvent/15% aqueous solution, immobilized on a hydrophilic solid support, labeled on the support, eluted, and analyzed. The second column from the right shows the result for the control (only water added to the deglycosylation mixture), and shows a peak area of close to 33 million units, close to the lower limit of the error bar for the control sample labeled in solution. The sample containing Tris buffer shows a peak area of approximately 26 million, a signal at least 10 times higher than that of the Tris-containing sample labeled in solution.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An in vitro method for labeling glycosylamines, and, optionally, for analyzing said labeled glycosylamines, said method comprising the following steps in the following order:

(a) obtaining glycosylamines in an aqueous solution, (b) mixing said aqueous solution in which glycosylamines are present with a quantity of organic solvent, thereby creating an organic solvent mixture composed of about 80% ±1% organic solvent, (c) passing said organic solvent mixture containing said glycosylamines through a porous solid support, thereby immobilizing said glycosylamines on said porous solid support while allowing reagents not immobilized on said porous solid support to pass though said porous solid support, and, (d) labeling said glycosylamines with an amine-reactive dye, either (1) while said glycosylamines remain immobilized on said porous solid support, and then eluting said labeled glycosylamines from said porous solid support with an aqueous solution into a container, or, (2) eluting said immobilized glycosylamines from said porous solid support with an aqueous solution into a container and then labeling said eluted glycosylamines with said amine-reactive dye, thereby labeling said glycosylamines.

2. The method of claim 1, wherein said porous solid support is made of a hydrophilic material and said organic solvent mixture is 80% +1% to 95% organic solvent to 20% +1% to 5% aqueous solution.

3. The method of claim 2, wherein said hydrophilic material is (a) cellulose, (b) glass fiber, (c) alumina, (d) silica, (e) a functionalized surface containing diol, aminopropyl, carbamoyl, cyanopropyl, ethylenediamine-N-propyl, (f) silica derivatized with diol, aminopropyl, or carbamoyl, (g) cellulose, (h) cyclodextrin, (i) aspartmamide, (j) triazole, (k) diethylaminoelthyl, (1) a resin used in solid phase extraction of carbohydrates, or, (m) a combination of two or more of these.

4. The method of claim 3, wherein said porous solid support is made of silica, said silica is covalently bonded to one or more carbamoyl groups, and said silica is in the form of beads or particles.

5. The method of claim 1, further comprising step (c'), washing said porous solid support with a solution that is 80 to 90% organic solvent and 20 to 10% aqueous solution, between steps (c) and (d).

6. The method of claim 1, further comprising step (e), separating said labeled glycosylamines by subjecting them to a separation method.

7. The method of claim 1, wherein said porous solid support has a surface of a non-hydrophilic material and said organic solvent mixture is at least 95% organic solvent.

8. The method of claim 7, in which said non-hydrophilic material is polyethylene, nylon, polyvinylidene fluoride, or polypropylene, and has pores or openings of 10 microns.

9. A kit for releasing N-glycans from a glycoprotein or glycopeptide as glycosylamines and then labeling with an amine-reactive dye said glycosylamines released from said glycoprotein or glycopeptide, said kit comprising:

a container containing a deglycosylation enzyme that releases N-glycans from glycoproteins or glycopeptides as glycosylamines, a container containing an aqueous solution suitable for incubating said deglycosylation enzyme with said glycoprotein or glycopeptide, a container containing an amine-reactive dye, a container containing an organic solvent, and a container having disposed within it a porous solid support of a hydrophilic material or having a hydrophilic surface.

10. The kit of claim 9, wherein said aqueous solution and said organic solvent are provided in pre-measured form such that, when combined, they form a mixture of organic solvent and aqueous solution that is 80-95% organic solvent to 20-5% aqueous solution.

11. The kit of claim 9, wherein said aqueous solution and said organic solvent are provided in pre-measured form such that, when combined, they form a mixture of organic solvent and aqueous solution that is 85% +2% organic solvent to 15% +2% aqueous solution.

12. The kit of claim 9, wherein said deglycosylation enzyme is PNGase F.

13. The kit of claim 9, wherein said amine-reactive dye is ((2-(diethylamino) ethyl 4-[(2,5-dioxopyrrolidin-1-yl)oxycarbonylamino]benzoate).

14. A kit for releasing glycosylamines from a glycoprotein or glycopeptide with a deglycosylation enzyme and labeling said released glycosylamines with an amine-reactive dye, said kit comprising:

a container containing a deglycosylation enzyme, a container containing a buffer, a container containing an amine-reactive dye, a container containing an organic solvent, and a container having disposed within it a porous solid support of a hydrophilic material or having a hydrophilic surface.

15. The kit of claim 14, further comprising a container containing a detergent.

16. The kit of claim 14, wherein said deglycosylation enzyme is PNGase F.

17. The kit of claim 14, wherein said amine-reactive dye is ((2-(diethylamino) ethyl 4-[(2,5-dioxopyrrolidin-1-yl) oxycarbonylamino]benzoate).

18. The kit of claim 14, wherein said organic solvent is acetonitrile, absolute ethanol, absolute methanol, isopropanol, butanol, toluene, ethyl acetate, acetone, tetrahydrofuran, diethyl ether, dichloromethane, chloroform, tert-buthylmethyl ether, benzene, carbon tetrachloride, isooctane, hexane, or a combination of any two or more of these.

19. The kit of claim 14, wherein said hydrophilic material of said porous solid or said hydrophilic surface of said porous solid support is of a hydrophilic material comprising (a) cellulose, (b) glass fiber, (c) alumina, (d) silica, (e) a functionalized surface containing diol, aminopropyl, carbamoyl, cyanopropyl, ethylenediamine-N-propyl, (f) silica derivatized with diol, aminopropyl, or carbamoyl, (g) cellulose, (h) cyclodextrin, (i) aspartmamide, (j) triazole, (k) diethylaminoelthyl, (1) a resin used in solid phase extraction of carbohydrates, or, (m) a combination of two or more of these.

20. The kit of claim 19, wherein said porous solid support is made of silica and said silica is covalently bonded to one or more carbamoyl groups.

* * * * *